United States Patent [19]
Gualtier

[11] Patent Number: 4,729,764
[45] Date of Patent: Mar. 8, 1988

[54] IRRIGATOR AND TISSUE SEPARATOR

[76] Inventor: Quentin E. Gualtier, 16 Winding Way, North Caldwell, N.J. 07006

[21] Appl. No.: 870,916

[22] Filed: Jun. 5, 1986

[51] Int. Cl.⁴ .............................................. A61M 5/18
[52] U.S. Cl. ...................................... 604/38; 604/152; 128/750; 128/765
[58] Field of Search ...................... 604/27–30, 604/36–38, 151–153; 128/750–765

[56] References Cited

U.S. PATENT DOCUMENTS

| | | | |
|---|---|---|---|
| 1,493,592 | 5/1924 | Beck | 604/36 |
| 1,925,230 | 9/1933 | Buckhout | 604/37 |
| 2,646,042 | 7/1953 | Quang Hsi Hu | 604/38 |
| 3,099,260 | 7/1963 | Birtwell | 604/153 |
| 3,892,226 | 7/1975 | Rosen | 604/37 |
| 3,993,061 | 11/1976 | O'Leary | 604/152 |
| 4,488,961 | 12/1984 | Spencer | 604/29 |

OTHER PUBLICATIONS

"Urological Instruments", A Comprehensive Guide to Purchasing (Catalogue) by V. Mueller & Co., 1963, 604/37.

Primary Examiner—C. Fred Rosenbaum
Assistant Examiner—Mario Costantino
Attorney, Agent, or Firm—S. A. Giarratana

[57] ABSTRACT

An irrigation device for injecting and withdrawing liquid from a body cavity, comprising a first chamber separated into two compartments by a partition provided with a one-way valve, wherein one compartment is operatively connected to a rolling diaphragm in combination with a piston member and the other compartment provided with a nozzle adapted to be coupled to a catheter already inserted in the body cavity.

A second chamber is removably attached to the first chamber with a gasket and filter member therebetween. With the device filled with irrigating liquid, manually pushing the piston member into the operatively connected compartment forces liquid through the one-way valve into the other compartment and through the nozzle and catheter into the body cavity. Retracting the piston member closes the one-way valve and liquid, as well as any particulate matter, is withdrawn from the body cavity into the second chamber and, in turn, through the filter member into the compartment operatively connected to the rolling diaphragm and piston member, and available for further irrigation of the body cavity. Particulate matter in the withdrawn liquid is retained in the second chamber and available for examination after the lavage.

1 Claim, 4 Drawing Figures

IRRIGATOR AND TISSUE SEPARATOR

FIELD OF INVENTION

The invention relates to an irrigator and tissue separator for injecting and withdrawing liquid from body cavities, as well as separating any particulate substance from the withdrawn liquid.

BACKGROUND OF THE INVENTION

Irrigation devices are commonly used in the medical field to flush a body cavity with a stream of liquid for facilitating lavage. For example, in urogolical surgery irrigation devices are generally utilized for washing out the urinary bladder with a suitable sterile liquid. In addition, a number of presently available devices remove particulate matter carried by the withdrawn liquid for examination by a laboratory.

Presently used irrigation devices may utilize an apparatus wherein the fluid is circulated through the body cavity by the compression and expansion of a syringe, of the type shown in U.S. Pat. Nos. 3,892,226 and 4,282,873 or an apparatus incorporating a number of coacting single action piston pumps as disclosed in U.S. Pat. No. 4,054,137.

A disadvantage of syringe type irrigation devices is the lack of sufficient and controllable pressure to efficiently and quickly circulate the fluid through the body cavity. Irrigation devices with piston pump mechanisms are generally complex in configuration and operation, in that such devices must be provided with accurately spaced and coacting inlet and outlet ports, as well as oppositely-working pistons.

OBJECTS OF THE INVENTION

An object of the present invention is to provide an improved device for irrigating and separating solids from liquid withdrawn from a body cavity.

Another object of the present invention is to provide an irrigation device with a minimum of moving parts which does not require expensive manufacturing or fabricating procedures.

Yet another object of the present invention is to provide an irrigation device which is simple in structural configuration, operation and cost.

A further object of the present invention is to provide an irrigation device which is capable of providing predetermined pressure control when liquid is injected or withdrawn from a body cavity.

BRIEF SUMMARY OF THE INVENTION

In accordance with the foregoing objects, the present invention is directed to a unitary housing provided with a pair of interconnecting chambers containing a suitable solution for irrigating a body cavity. The first or upper chamber is separated into two compartments by a partition provided with a one-way valve. One compartment is operatively connected to a rolling diaphragm apparatus, comprising a rolling diaphragm associated with a piston within a cylindrical member, and the other compartment provided with an integral nozzle for attaching to a catheter sheath. The second or lower chamber is removably connected to the first chamber with a gasket member therebetween provided with a restricted orifice, to minimize irrigating liquid from back-flowing into the first chamber from the second chamber as well as restricting the flow rate into the second chamber, and with a plurality of filtering apertures to separate particulate matter from liquid withdrawn from a body cavity for retention in the lower chamber.

In operation, the piston is initially retracted so that the rolling diaphragm is unrolled from the surface of the piston and irrigating liquid placed within the irrigator, through the top of the first chamber, to substantially fill the two compartments in the first chamber and the second chamber. By pushing the piston within the cylinder body, with a manual force appropriate to the particular application, the pressure created by the rolling diaphragm apparatus opens the one-way valve and forces the irrigating liquid displaced by the piston through the nozzle and catheter sheath into the body cavity. When the piston is retracted, the one-way valve immediately closes and the liquid, as well as any particulate matter, is withdrawn from the body cavity. The withdrawn irrigating liquid is directed from the compartment in the first chamber, through the restricted orifice into the second chamber and, in turn, through the filtering apertures into the compartment operatively connected to the rolling diaphragm apparatus. This configuration of the gasket member, with its integral restricted orifice and filtering apertures, retains particulate matter in the withdrawn liquid within the second chamber. After the desired cycles of injecting the withdrawing the liquid is completed the second chamber is removed from the irrigator and any particulate matter therein sent to the laboratory for examination. Thereafter, the irrigator device is discarded.

DESCRIPTION OF THE DRAWINGS

In all views, like numbers designate like parts.

DESCRIPTION OF THE INVENTION

Figure 1:
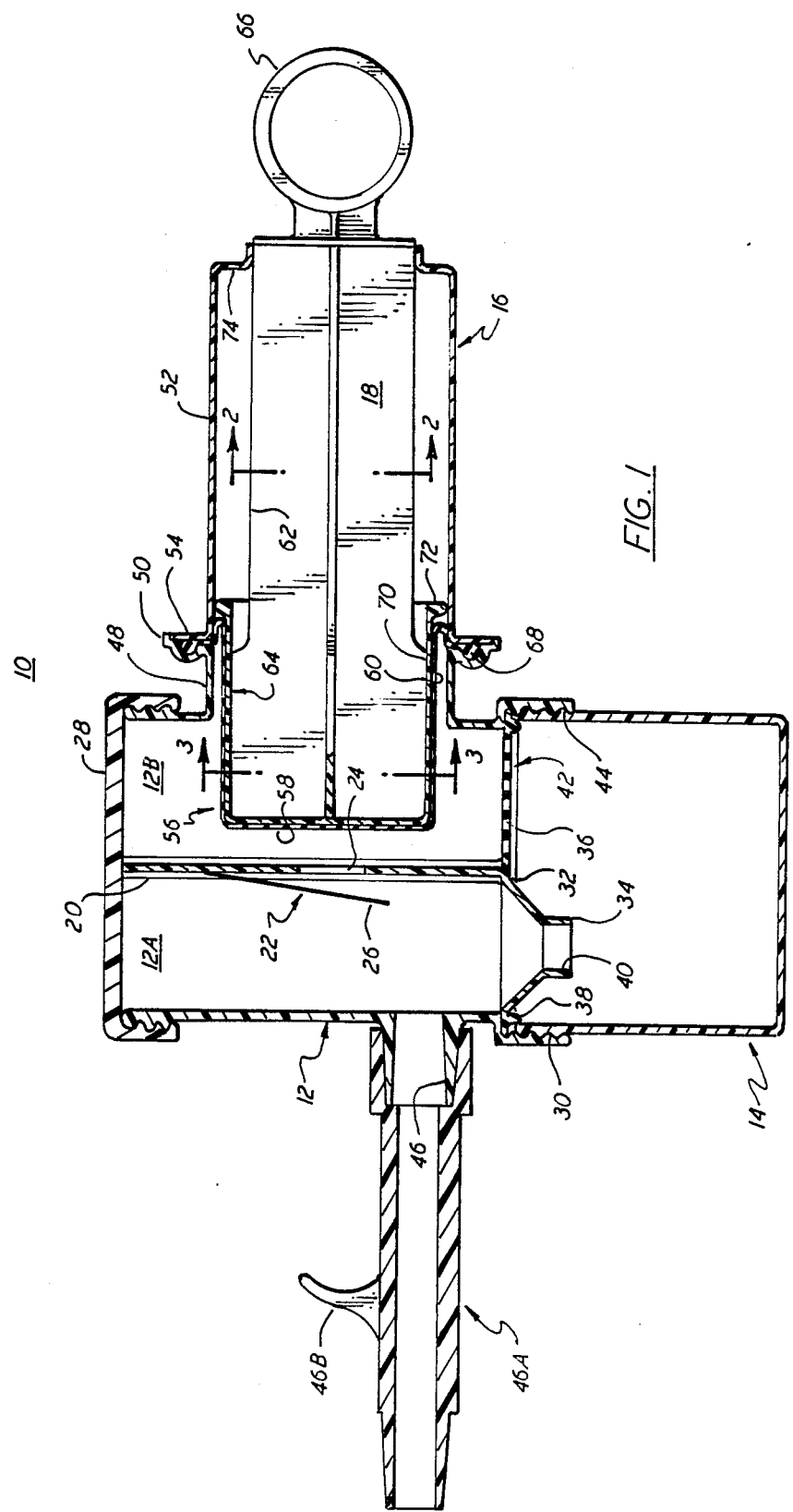
FIG. 1 is a side view of a preferred embodiment of the present invention.

Referring to FIG. 1, there is shown an irrigating and waste separating device made in accordance with the principles of the present invention which in a preferred embodiment 10 comprises a first chamber 12, a second chamber 14 detachably secured thereto, and a rolling diaphragm apparatus 16, having a piston member 18, operatively attached to the first chamber. The chambers and the piston assembly may be of a relatively rigid and impervious material, such as plastic or glass, chosen on the basis of chemical and biological inertness and compatability with the standard methods of sterilization. The dimensions of the device are such that the operatively coupled chambers and piston assembly are held in one hand and the piston plunger 18 operated with the other hand.

The first chamber 12 is shown as a substantially cylindrical member fabricated with a partition wall 20 dividing the chamber into two approximately equal compartments 12A and 12B. The wall is provided with a one-way valve assembly 22 consisting of an aperture 24, commonly referred to as a valve port, and an operatively coacting flap valve 26, fabricated from a suitable resilient material, such as a synthetic rubber substitute or the like, and having an area sufficient to seat and seal against the valve port, to thereby prevent the passage of liquid therethrough. The flap valve 26, operatively located within compartment 12A, permits a one-way flow of liquid through the valve port 24 from compartment 12B into compartment 12A. The open top end of the chamber is provided with a closure member, such as threaded cap 28, to seal said chamber 12 during the irrigation process. The cap also serves as closure member for the second chamber after the completion of the irrigation process, as hereinafter described. The first chamber's open bottom end is provided with an internally threaded, integral flange 30 for removably threading the second chamber thereto.

An integral gasket and filter member 32, fabricated with a restricted orifice 34 and, radially spaced therefrom, a plurality of either round or square filtering apertures 36, is provided between the first and second chambers. The member 32 is fabricated with its peripheral edge adapted to serve as a sealing gasket 38 between the first and second chambers, to prevent leakage therebetween during the irrigation process. Filtering apertures 36 are provided in sufficient number between compartment 12B and chamber 14 to filter substantially all particulate matter in the irrigating solution flowing therethrough. In the present invention, the withdrawn liquid from the body cavity containing tissue and other particulate substance will be prevented by the filtering apertures 36 from entering compartment 12B, remaining in the second chamber 14 for later examination after the lavage of the body cavity. The restricted orifice 34 is located between the compartment 12A and chamber 14, and is to define a narrow opening 40 tapered in the downward direction protruding into the chamber 14.

The cup-shaped chamber 14 is provided adjacent its open end 42 with external threads 44 adapted to removably engage the internally threaded flange 30 of chamber 12. The gasket and filter member 32 is operatively maintained between the open bottom end of chamber 12 and the open top end of chamber 14 by operatively engaging the external thread 44 of chamber 14 with the internally threaded flange 30 of chamber 12, until the chambers are securely attached together with the member 32 therebetween. In the preferred embodiment, it is obvious that the threads of the flange 30 and the external threads 44 of chamber 14 are configured to operatively engage each other; and in like manner, the threads of the cap member 28 are dimensioned to operatively engage external threads 44.

Chamber 12 is provided with an outlet-inlet nozzle 46 integral with and in open communication with compartment 12A. A nozzle extension 46A is attached to the nozzle 46, such as solvent cemented thereto, for establishing a suitable liquid connection between the preferred embodiment 10 and a catheter sheath (not illustrated). In turn, the catheter is inserted into the interior of a body cavity (not illustrated). A vertical flange 46B is provided on the nozzle extension 46A as an aid in holding the preferred embodiment 10, as hereinafter disclosed. In addition, chamber 12 is fabricated with an outwardly projecting cylindrical flange 48 having an axis substantially perpendicular to the axis of said chamber and substantially co-axial with the axis of the valve port 24. The flange 48 is formed with an integral, peripheral clamping surface 50 for attaching thereto, as hereinafter disclosed, the rolling diaphragm apparatus 16.

The apparatus 16 comprises a cylindrical housing 52 having the same internal radius as the cylindrical flange 48 and formed with an integral, radially projecting clamping flange 54. The piston 18 is movably arranged within said cylindrical housing, and a rolling diaphragm 56 operatively associated with the piston. The rolling diaphragm is formed from any suitable material having an inherent resilience, such as a synthetic rubber substitute characterized by resistance to any chemical reaction with any irrigating solution or bodily fluids. The diaphragm is fabricated substantially as a tube member having a flat closed end 58 and a radially flared skirt 60, comprising the rolling wall portion of the diaphragm. The piston 18 consists of piston rod 62 having an integral piston head 64 at one end and a handle 66 at the opposite end for manually manipulating the piston. The cylindrical housing 52 is securely attached to the cylindrical flange 48 by mating the clamping flange 54 with the peripheral clamping surface 50. In addition, the peripheral end of the flared skirt 60 of the diaphragm is also clamped between the clamping flange 54 and the clamping surface 50, with suitable sealing means, such as O-ring 68, formed as an integral part of the rolling diaphragm 56 and provided for effecting a liquid tight seal between the cylindrical housing 52 and the chamber 12. The flat closed end 58 of the diaphragm is suitably attached in any conventional manner to the end of the piston head 64. From the foregoing, it is understood that the rolling diaphragm prevents any leakage of the liquid from the upper and lower chambers into the cylindrical housing 52 during the operation of the preferred embodiment 10. The piston 18 is configured to be movable between two limit positions. FIG. 1 shows the piston in its fully extended position in which the outer peripheral surface 70 of the piston head 64 is substantially engaged by the rolling wall portion of the rolling diaphragm. The limit position of the piston when retracted is determined by the axial inner end 72 of the piston head contacting the inwardly projecting radial end flange 74 of the cylindrical housing 52.

Figure 4:
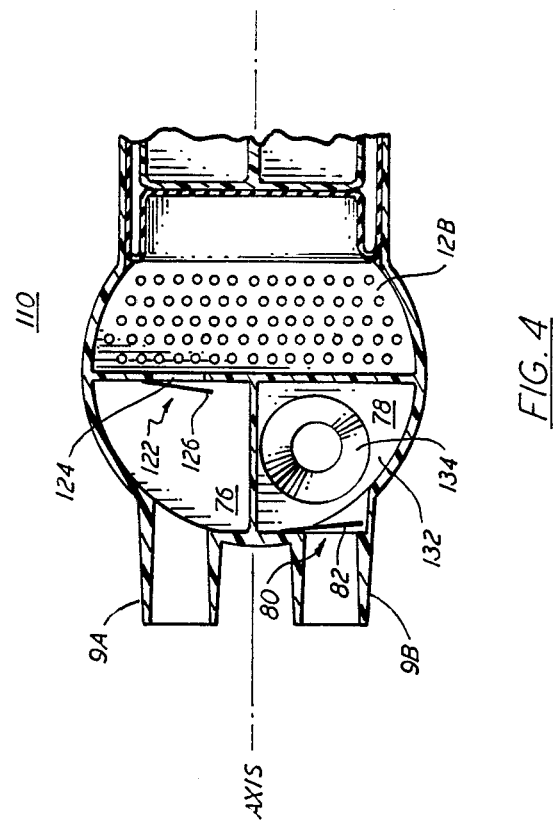
FIG. 4 is a view, in horizontal section, of a modified form of the preferred embodiment of FIG. 1.
Figure 2:
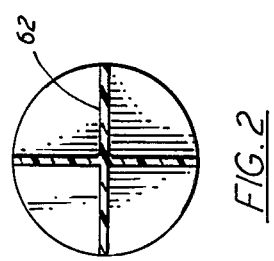
FIG. 2 is a section view taken substantially in the plane of line 2—2 on FIG. 1, and showing a cross-section of the piston plunger.
Figure 3:
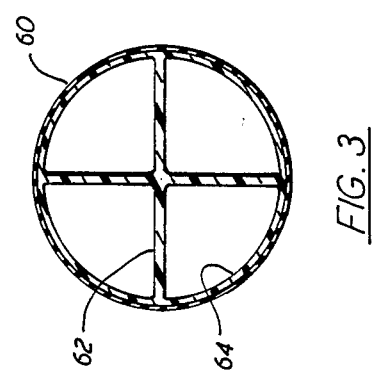
FIG. 3 is a section view taken substantially in the plane of line 3—3 on FIG. 1, and showing a cross-section of the piston head.

FIG. 4 discloses a modification 110 of the subject irrigator and tissue separator device wherein compartment 12A of the preferred embodiment 10 is divided substantially into two smaller compartments, specifically, an out-flow compartment 76 and an in-flow compartment 78. The out-flow compartment is operatively connected to compartment 12B by a one-way valve assembly 122 consisting of a valve port 124 and flap valve 126. Compartments 76 and 78 are provided with flow nozzles 9A and 9B, respectively, adapted to engage catheters for establishing one path for injecting liquid into the body cavity and another for the liquid removed from the same body cavity. The in-flow compartment 78 is operatively connected to the second chamber 114 by a restricted orifice 134 provided in the gasket and filter member 132. To prevent the back flow of liquid from the in-flow compartment 78 through the nozzle 9B, a one-way valve assembly 80 is provided adjacent the inner end of the nozzle, with a flap valve 82 having an area sufficient to seat and seal against the said inner end of the nozzle. The remaining structure and function of the modification 110 is identical to the structure and function of the preferred embodiment 10.

It will be appreciated that the modification 110 is adapted to be used when desirable to accomplish lavage without reversal of liquid flow direction and with continuous removal of particulate matter from the recirculating liquid.

In operation, the top member 28 of the device 10 is unscrewed from the top of the chamber 12 and with the piston 18 fully retracted and the nozzle extension 46A attached to a catheter sheath, already inserted into the body cavity, all portions of the subject device are filled completely with a sterile liquid or the device may be backfilled with the fluid remaining in the body cavity as a result of a surgical procedure. With the cap member replaced, the preferred embodiment is held to the sheath, not shown, by applying pressure with the thumb of one hand to the vertical flange 46B of the nozzle extension 46A, while the other hand operates the piston member by means of the piston handle 66. Accordingly, the piston with the rolling diaphragm 56 attached thereto is manually pushed forward and the pressure created within the device as a result of the piston head 64 displacing fluid therein opens the flap valve 26 and liquid forced through the valve port 24 and nozzle 46 through the catheter into the body cavity. When the piston is retracted, immediately the flap valve 26 seats and seals the valve port 24 and the liquid is withdrawn back into compartment 12A together with any particulate matter. The partition wall 20 forces the liquid to flow through the restricted orifice 34 into the chamber 14 and, in turn, through the filtering apertures 36 into compartment 12B, ready to be recirculated. However, substantially all particulate matter in the circulating liquid is retained in chamber 12 by the filtering aperture. When the lavage is completed, the chamber 14 is unscrewed from chamber 12 and with the particulate matter therein, sealed with the cap member 28. Other than the sealed chamber 14, the rest of the device is discarded.

It should be understood that the piston 18 enables the operator to control the flow pressure of the liquid and, in turn, the degree of agitation of the liquid during lavage. Also, the restricted orifice 34 is configured to minimize the flow of any particulate matter from chamber 14 back into chamber 12 and, since the filtering apertures 36 prevents the passage of particulate matter into compartment 12B, the recirculating liquid is substantially free of said particulate matter. It should be noted that as the piston head 64 is moved forward into the compartment 12B, although substantially the entire flow of fluid displaced by the piston head is through the valve port 24, there may be some movement of fluid from compartment 12B through the filtering apertures 36 and back again from chamber 14 into compartment 12B until all the fluid displaced by the piston head is injected into the body cavity through nozzle 46. This back and forth movement of fluid through the filtering apertures is desirable since it minimizes the clogging, if any, of the filtering apertures. The operation of the modification 110 differs from the preferred embodiment 10, in that a substantially continuous flow is generated through the body cavity. In brief, as in the preferred embodiment, with the piston 18 fully retracted, all portions of the modification 110 are filled completely with a sterile liquid and the cap member threadedly replaced. In operation, as the piston 18 is moved inwardly, the rolling diaphragm 56 unfolds along the outer peripheral surface 70 of the piston head 64 causing the volume in the compartment 12B to be decreased and sterile liquid accordingly to be displaced out through the valve port 124 and, in turn, through the nozzle 9A into the catheter, not shown. It should be understood, that since the peripheral end of the flared skirt portion 60 of the diaphragm is firmly held in compression uniformily about its periphery between the clamping surface 50, of the cylindrical flange 48, and the clamping flange 54, of the cylindrical housing 52, the only outlet for the liquid is the nozzle 9A. Also, since the piston head 64 is capable of displacing a large volume of liquid, relative to the total volume of the compartment 12B, when the piston is fully extended, a large volume of liquid is displaced out through the nozzle 9A with each operation of the piston 18. Additionally, as the piston is retracted, a relatively large amount of negative pressure is generated within the device 110 causing the flap valve 126 to immediately seal the valve port 124 to stop the flow through nozzle 9A. The negative pressure enhances the withdrawal of liquid from the body cavity and through nozzle 9B and, in turn, through the restricted orifice 134 and the filtering apertures 136, thereby evacuating the body cavity quickly, completely and efficiently. It should be understood that the irrigator procedure is repeated as many times as necessary, by filtering and recirculating the same liquid, to properly flush out the body cavity of particulate matter.

It will be understood that various changes may be made in the apparatus described without departure from the principles of the invention. Accordingly, it is intended that all matter contained in the above description and shown in the accompanying drawings shall be interpreted as illustrative and not in a limiting sense.

What is claimed is:

1. An irrigation device for injecting fluid into and withdrawing fluid from a body cavity and separating solids from liquid withdrawn from the body cavity, which irrigation device comprises
    (a) a cylindrical housing defining first and second juxtaposed chambers each extending along the length of said housing in the axially elongated direction, said housing defining an open top and bottom end, said housing further defining a cylindrical flange extending outwardly from the cylindrical wall defining said second chamber and having an open end in direct communication with said second chamber, said flange having an axis perpendicular to the axis of said housing and defining a peripheral clamping surface at its open end extending outwardly and parallel to the axis of said housing;
    (b) a cup member axially and removably attached to the open bottom end of said housing and defining a reservoir therein for receiving fluid from said housing;
    (c) a cap member removably attached to the open top end of said housing for closing said top end of said housing;
    (d) a one-way valve assembly provided between said first and second juxtaposed chambers for permitting the flow of fluid through said valve assembly only in the direction from said second chamber to said first chamber;
    (e) a nozzle member integral with said housing for permitting inlet and outlet flow through said first chamber of said housing for fluid within said device;
    (f) a removable, integral gasket and filter member between said housing and said cup member, said gasket and filter member comprising peripheral sealing means for preventing fluid from leaking from said device between said cup member and said housing, said gasket and filter member defining a downwardly tapered orifice for permitting the flow of fluid from said first chamber to said reservoir and for restricting back-flow of fluid from said cup member into said chamber, said gasket and filter member further defining a plurality of filtering apertures radially spaced from said orifice and arranged between said reservoir and said second chamber for preventing solids in the fluid within said reservoir from entering said second chamber; and (g) a rolling diaphragm apparatus comprising a cylindrical member defining at one end thereof a radially projecting clamping flange and defining an opening at the other end, and wherein said clamping flange is connected to said peripheral clamping surface of said cylindrical flange of said housing, said cylindrical member being arranged coaxial with said cylindrical flange, said rolling diaphragm further comprising a piston head coaxially arranged within said cylindrical member, and a rolling diaphragm having a flat closed end attached to the side of said piston head facing said housing, said rolling diaphragm further including a radially flared skirt projecting outwardly from said flat closed end and defining a peripheral end formed as an O-ring, said peripheral O-ring end held in compression between said clamping flange of said cylindrical member and said clamping surface of said cylindrical flange of said housing, said flared skirt forming a fluid tight seal with said cylindrical flange for preventing leakage of fluid from said cylindrical housing and said cup member into said cylindrical member of said rolling diaphragm apparatus, said rolling diaphragm apparatus further comprising a piston rod connected to the other side of said piston head and coaxial therewith, said rod projecting outwardly through said open end of said cylindrical member for manually manipulating said piston rod to axially reciprocate said piston rod within said cylindrical member, and in turn, reciprocate said piston head and said rolling diaphragm within said second chamber of said housing, whereupon on the inward stroke of said piston rod, said piston head and rolling diaphragm displaces fluid from said second chamber through said one-way valve assembly into said first chamber, and in turn, further injects fluid into the body cavity through said nozzle member, and alternatively, the outward stroke of said piston rod withdraws said piston head from said second chamber, and in turn, positively draws fluid from the body cavity back through said nozzle member into said first chamber, and further through said restricted orifice into said reservoir, and then draws fluid from said reservoir through said filtering apertures into said second chamber, for further recirculation of fluid through the device and body cavity by alternately introducing at predetermined intervals said piston head in and out of said chamber.

* * * * *